United States Patent [19]

Miyake et al.

[11] Patent Number: 4,797,395
[45] Date of Patent: Jan. 10, 1989

[54] 1-ACYLOXYALKYL ESTERS OF CEPHALOSPORIN

[75] Inventors: Akio Miyake; Yoshinobu Yoshimura; Mitsuo Numata, all of Osaka, Japan

[73] Assignee: Takeda Chemical Industries, Ltd., Osaka, Japan

[21] Appl. No.: 886,814

[22] Filed: Jul. 18, 1986

Related U.S. Application Data

[63] Continuation of Ser. No. 616,402, Jun. 1, 1984, abandoned.

[30] Foreign Application Priority Data

Jun. 2, 1983 [JP] Japan ................... 58-99213
Sep. 21, 1983 [JP] Japan ................... 58-175496

[51] Int. Cl.$^4$ ................... A61K 31/545; C07D 501/36
[52] U.S. Cl. ...................... 514/206; 540/227
[58] Field of Search ........................ 540/227; 514/206

[56] References Cited

U.S. PATENT DOCUMENTS 4,497,809  2/1985  Yoshimura et al. ............ 540/227 X
4,593,115  1/1986  Miyake et al. ................. 560/123 X
4,616,008 10/1986  Hirai et al. ..................... 514/777 X
4,729,992  3/1988  Nishimura et al. ............ 540/227 X

FOREIGN PATENT DOCUMENTS 135791 10/1979 Japan .

Primary Examiner—Donald G. Daus
Assistant Examiner—William A. Tioli, Jr.
Attorney, Agent, or Firm—Antonelli, Terry & Wands

[57] ABSTRACT

A compound of the formula

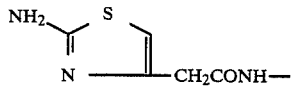
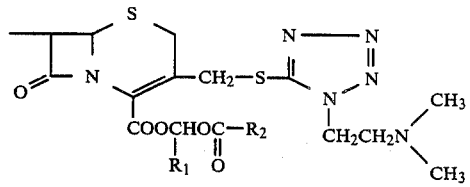

wherein (1) $R_1$ is a lower alkyl group of 2 to 6 carbon atoms or a cycloalkyl group of 5 to 7 carbon atoms and $R_2$ is a cycloalkyl group of 5 to 7 carbon atoms or a lower alkyl group of 1 to 3 carbon atoms which is substituted by a cycloalkyl group of 5 to 7 carbon atoms or by a phenyl group, or (2) $R_1$ is a cycloalkyl group of 5 to 7 carbon atoms and $R_2$ is a lower alkyl group of 1 to 5 carbon atoms, or a pharmacetically acceptable salt thereof, processes for preparing the same and a pharmaceutical composition thereof are provided. The compound can orally be applied as antibiotics having improved bioavailability.

6 Claims, No Drawings

1-ACYLOXYALKYL ESTERS OF CEPHALOSPORIN

This is a continuation of application Ser. No. 616,402, filed June 1, 1984 now abandoned.

This invention relates to compounds of the general formula:

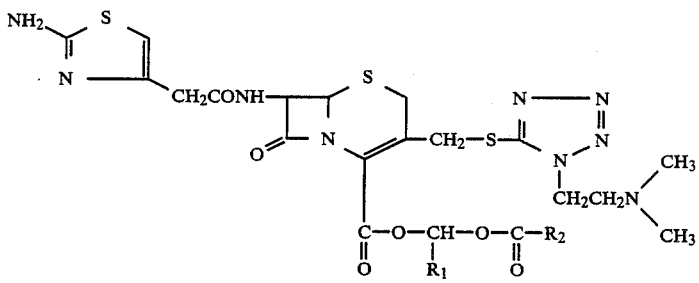

[I]

wherein (1) $R_1$ is a lower alkyl group of 2 to 6 carbon atoms or a cycloalkyl group of 5 to 7 carbon atoms, and $R_2$ is a cycloalkyl group of 5 to 7 carbon atoms or a lower alkyl group of 1 to 3 carbon atoms which is substituted by a cycloalkyl group of 5 to 7 carbon atoms or by a phenyl group, or (2) $R_1$ is a cycloalkyl group of 5 to 7 carbon atoms and $R_2$ is a lower alkyl group of 1 to 5 carbon atoms, or a pharmaceutically acceptable salt thereof.

For promoting the absorption, on oral administration, of 7β-[2-(2-aminothiazol-4-yl)acetamido]-3-[[[1-(2-dimethylaminoethyl-1H-tetrazol-5-yl]thio]methyl]-ceph-3-em-4-carboxylic acid (described in U.S. Pat. No. 4,080,498, common name: cefotiam, hereinafter referred to briefly as compound [II]), it has been suggested to convert the compound [II] into pivaloyloxymethyl ester thereof or a straight-chain or branched alkyl or alkoxycarbonyloxy substituted alkyl ester thereof (e.g. U.S. Pat. No. 4,189,479, EP-93548A and Japanese published unexamined patent application No. 77690/1982). However, these esters have still much to be desired in the respect of absorbability, stability, etc.

The present inventors conducted an intensive study of various ester derivatives of the compound [II] succeeded in the synthesis of the aforementioned novel compound [I] (referred to sometimes as the ester hereinafter) and found that the above novel compound [I] is efficiencly absorbed from the gastrointestinal tract and, after absorption, quickly transferred into the blood stream in the form of non-ester of the compound [I] (i.e. compound [II]) to establish a high blood level of non-ester of the compound [I] so that it is of value as an orally administrable broad-spectrum antibiotic displaying potent inhibitory effects not only against gram-positive and gram-negative bacteria but also against resistant strains thereof. It was also found that the salt of the compound [I] has an improved water solubility and a better absorption-efficiency of compound [I] and facilitates the procedures of isolation, stabilization and processing into pharmaceutical preparations of the antibiotic.

Referring to the compound [I] of this invention, (1) $R_1$ is a straight-chain or branched lower alkyl group of 2 to 6 carbon atoms such as ethyl, n-propyl, isopropyl, n-butyl, isobutyl, t-butyl, n-pentyl, isopentyl, neopentyl, t-pentyl, n-hexyl, and iso-hexyl or a cycloalkyl group of 5 to 7 carbon atoms such as cyclopentyl, cyclohexyl and cycloheptyl, and $R_2$ is a cycloalkyl group of 5 to 7 carbon atoms such as cyclopentyl, cyclohexyl and cycloheptyl, or a lower alkyl group containing 1 to 3 carbon atoms such as methyl, ethyl, n-propyl and iso-propyl, which is substituted by a cycloalkyl group of 5 to 7 carbon atoms such as cyclopentyl, cyclohexyl and cycloheptyl or by a phenyl group; (2) $R_1$ is a cycloalkyl group of 5 to 7 carbon atoms such as cyclopentyl, cyclohexyl and cycloheptyl,and $R_2$ is a lower alkyl group of 1 to 5 carbon atoms such as methyl; ethyl, n-propyl, isopropyl, n-butyl, iso-butyl, sec-butyl, tert-butyl, n-pentyl, 3-methylbutyl, 2-methylbutyl, 1-methylbutyl, 2-ethylpropyl, 3-ethylpropyl, 1,2-dimethylpropyl, etc. Preferred are compounds in which (1) $R_1$ is ethyl, n-propyl or isopropyl and $R_2$ is cyclopentyl, cyclohexyl, cyclohexylmethyl or benzyl; or (2) $R_1$ is cyclohexyl and $R_2$ is n-butyl or n-propyl.

More preferably, (1) $R_1$ is ethyl, n-propyl, isopropyl or cyclohexyl and R2 is cyclohexyl, cyclohexylmethyl or benzyl, and (2) Rl is cyclohexyl and R2 is n-butyl, n-propyl or 2-methylpropyl.

Since the compound [I] is basic in itself, it can be converted into an acid addition salt thereof. Generally, 1 mole of the compound [I] forms an acid addition salt with 1 or 2 moles of an acid. Acids which are preferably employed for the formation of such acid addition salts include those known to form pharmaceutically acceptable salts with pencillins and cephalosporins; for example, inorganic acids such as hydrochloric acid, sulfuric acid, phosphoric acid, etc. and organic acids such as maleic acid, acetic acid, citric acid, succinic acid, tartaric acid, malic acid, malonic acid, fumaric acid, benzoic acid, mandelic acid, ascorbic acid, methanesulfonic acid, etc.

Preferred salts of the compound [I] are the monohydrochloride and dihydrochloride. The most desirable is the dihydrochloride. The aminothiazole group of the compound [I] or a salt thereof may exist in the form of its tautomer i.e. iminothiazoline. As the compound [I] or a salt thereof has an asymmetric carbon in the carboxyl ester group at 4-position of the cephem nucleus, there exist two optically active forms (D-isomer and L-isomer). The compound [I] or a salt thereof can generally be used as a racemic compound but either the D-isomer or L-isomer or mixture of such optical isomers can also be employed. The compound [I] or a salt thereof is absorbed well through the gastro-intestinal tract and after absorption the ester moiety at its 4-carboxyl position is promptly hydrolyzed with enzyme in the body to give the non-ester form of compound [I], which is the compound [II].

The compound [II] has strong antibacterial activity as mentioned in Antimicrobial Agent and Chemotherapy 14, 557–568 (1978). Thus, the compound [II] displays potent antibacterial activity against gram-positive bacteria such as *Staphylococcus aureus*, etc. and gram-negative bacteria such as *Escherichia coli, Klebsiella pneumoniae, Proteus vulgaris, Proteus mirabilis* and *Proteus morganii*.

Since the compound [I] or a salt thereof, when administered by the oral route, gives a high concentration of the compound [II] in the blood, it is effective in the treatment of infections due to said bacteria in man and other mammalian animals, such as respiratory tract and urinary tract infections due to said bacteria.

The compound [I] or a salt thereof is low in toxicity ($LD_{50} \geq 3$ g/kg, mice, p.o.) and can be orally administered. Therefore, in combination with per se known pharmaceutically acceptable excipients (e.g. starch, lactose, calcium carbonate, calcium phosphate, etc.), binders (e.g. starch, gum arabic, carboxymethylcellulose, hydroxypropylcellulose, crystalline cellulose, etc.), lubricants (e.g. magnesium stearate, talc, etc.) or/and disintegrating agents (e.g. carboxymethylcalcium, talc, etc.), the compound [I] or a salt thereof can be formulated into such dosage forms as capsules, powders, fine granules, granules, tablets, etc. It is also possible to add about 1 to 5 mole equivalents of a solid organic acid (e.g. citric acid, malic acid, tartaric acid, succinic acid, ascorbic acid, mandelic acid, etc.) to the compound [I] or a salt thereof and mold the mixture into granules in a conventional manner. Such granules can be further processed into capsules, tablets, etc. by the established pharmaceutical procedures.

With regard to the dosage regimen, the compound [I] or a salt thereof can be administered at a daily dose of 0.3 to 5 g per adult human, preferably 0.5 to 3 g per adult human divided into 3 or 4 equal doses.

The compound [I] or a salt thereof can be produced by per se known processes (for example, the processes described in the specifications of U.S. Pat. No. 4,080,498, U.S. Pat. No. 4,189,479 and Japanese published unexamined patent application No. 77690/1982. Moreover, the compound [I] or a salt thereof can be produced by esterifying the compound [II] or a salt thereof with a compound of the general formula:

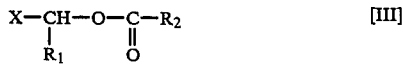

[wherein X is a halogen atom; $R_2$ has the same meaning as defined hereinbefore].

Referring to the above general formula [III], the halogen atom represented by X is for example chlorine, bromine and iodine. Of these species, X is preferably iodine for the purpose of esterification.

As the compound [III] has an asymmetric carbon atom, it can be optically resolved into D- and L- isomers by a per se known procedure and either of the isomers or a mixture thereof can be used in the contemplated esterification reaction.

The starting compound [II] can be subjected to the reaction in the form of an acid addition salt with an inorganic acid such as hydrochloric acid, sulfuric acid and nitric acid, or an organic acid such as oxalic acid and p-toluene-sulfonic acid, or in the form of a salt with a base such as an alkali metal, e.g. sodium, potassium, etc., an alkaline earth metal, e.g. calcium, magnesium, etc., or an organic amine, e.g. triethylamine, trimethylamine, pyridine, collidine, lutidine, etc.

In conducting the esterification reaction, the starting compound [III] is used in a proportion of about 1 to 2 mole equivalents to each equivalent of the starting compound [II] or a salt thereof.

This reaction is generally carried out in a solvent inert to the reaction. Suitable species of such solvent include amides such as N,N-dimethylformamide (hereinafter referred to briefly as DMF), N,N-dimethylacetamide (hereinafter referred to briefly as DMAC), hexamethylphosphorotriamide (hereinafter referred to briefly as HMPA), etc., halogenated hydrocarbons such as dichloromethane, chloroform, etc., sulfoxides such as dimethyl sulfoxide (hereinafter referred to briefly as DMSO), sulfolane, etc., ethers such as dioxane, tetrahydrofuran (hereinafter referred to briefly as THF), ketones such as acetone, methyl ethyl ketone, etc., nitriles such as acetonitrile, etc., liquefied sulfur dioxide, and so forth. Preferred are DMF, DMAC, HMPA, acetone, acetonitrile, liquefied sulfurdioxide, etc. This esterification reaction is conducted generally at a temperature between about $-20°$ C. and $20°$ C. While the reaction can be conducted in the absence of a catalyst, a catalyst such as a phase transfer catalyst (e.g. 18-crown-6, etc.) can be employed. When liquefied sulfurdioxide is used as the solvent, the reaction is preferably conducted at a temperature near the boiling point ($-10°$ C.) of the solvent, i.e. about $-10°$ C. to $-20°$ C. The reaction time is generally 10 minutes to about 6 hours, depending on the species of reactants and solvent, etc.

The compound [I] or a salt thereof can also be produced by the following and other processes. Thus, a compound of the general formula

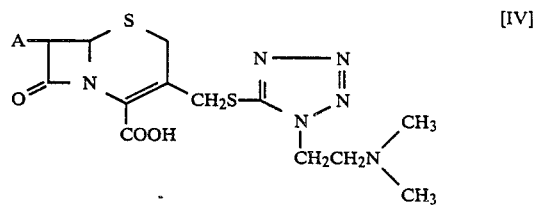

[wherein A is an amino group or an acylamino group other than 2-(2-aminothiazol-4-yl)acetylamino] or a salt thereof is reacted with the compound [III] in the same manner as the above-described esterification reaction and when A is an acylamino group, the resulting ester is reacted with phosphorus pentachloride and, then, with alcohol (e.g. methanol, ethanol, propanol, isopropanol, n-butanol, etc.) the process described in Journal of Medicinal Chemistry 18, 992 (1975), and West German Laid-open patent application Nos. 2460331 and 2460332]. The resulting compound of the general formula:

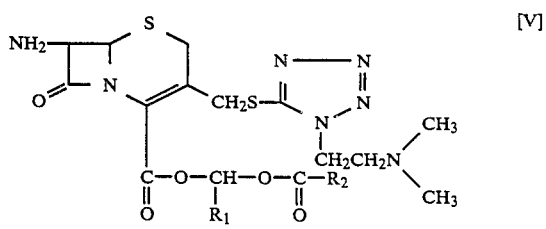

[wherein symbols have the same meanings as defined hereinbefore] or a salt thereof is acylated with 2-(2-aminothiazol-4-yl) acetic acid of the formula:

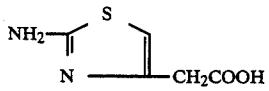

or a reactive derivative thereof, to give the compound [I] or a salt thereof.

Referring to the above general formula [IV], when A is an acylamino group, the acyl group can be any of the acyl groups known per se in the field of cephalosporin compounds. Preferred species of such acylamino group are acetylamino, benzoylamino, phenylacetylamino, thienylacetylamino, phenyloxyacetylamino and 5-amino-5-carboxyvalerylamino (the substituent amino group may be protected with phthaloyl or the like). When A is an amino group or an amino-substituted acylamino group, the substituent amino group is preferably protected before the reaction and the protective group therefor may for example be per se known protective groups for an amino group, such as t-butoxycarbonyl, carboxybenzyloxy, 2-hydroxy-1-napthocarbonyl, trichloroethoxycarbonyl, 2-ethoxycarbonyl-1-methylvinyl, or 2-methoxycarbonyl-1-methylvinyl.

The deacylation of the ester compound produced by reacting the compound [IV] (when A is an acylamino group) with the compound [III] is conducted in a per se known manner, using generally about 2 to 5 mole equivalents of phosphorus pentachloride and about 10 to 40 mole equivalents of alcohol per mole of the starting ester compound. This reaction is generally conducted in an inert solvent such as halogenated hydrocarbons, e.g. dichloromethane, chloroform, etc. For the purpose of accelerating the reaction, a tartiary amine such as triethylamine, pyridine, N,N-dimethylaniline may be added to the reaction system. The reaction temperature is about $-40°$ C. to about $-20°$ C. The reaction time is usually about 1 hour.

When the resulting compound [V] or a salt thereof is reacted with the compound [VI] or a reactive derivative thereof, to produce the compound [I] or a salt thereof, the amino group of the compound [VI] is preferably protected beforehand and the protective group can be similar to the protective group for the amino group of the compound [IV]. In this reaction, the compound [VI] may be used in the form of a reactive derivative. Thus, for example, it is subjected to said acylation reaction in the form of the corresponding acid halides, acid anhydrides, mixed acid anhydrides, active amides, active esters, etc. Preferred are the active esters, mixed acid anhydrides, acid halides etc. Examples of such active esters are p-nitrophenyl ester, 2,4-dinitrophenyl ester, pentachlorophenyl ester, N-hydroxyphthalimide ester, and the ester formed by means of a Vilsmeier or similar reagent and so on. The mixed acid anhydrides are those prepared from carbonic mono esters such as monomethyl carbonate, monoisobutyl carbonate, etc., and those prepared from alkanoic acids of 2 to 5 carbon atoms which may be substitued by halogens, such as pivalic acid, trichloroacetic acid, etc. Examples of such acid halides are acid chloride, acid bromide etc.

In this reaction, the compound [VI] or a reactive derivative thereof is used in a proportion of about 1 to 2 mole equivalents to each mole equivalent of the compound [V] or a salt thereof.

When the compound [VI] is used in the form of the free acid or a salt thereof, a suitable condensing agent is employed. Examples of such suitable condensing agent include N,N'-di-substituted carbodiimides such as N,N'-dicyclohexylcarbodiimide, azolides such as N,N'-carbonylimidazole, N,N'-thionyldiimidazole, etc., and such dehydrating agents as N-ethoxycarbonyl-2-ethoxy-1,2-dihydroquinoline, phosphorus oxychloride, alkoxyacetylenes (e.g. ethoxyacetylene) and so on. When such a condensing agent is employed, the reaction appears to proceed via formation of a reactive derivative of the carboxylic acid.

Generally this reaction can be smoothly conducted in a solvent. Examples of the solvent include the common solvents which do not interfere with the contemplated reaction, such as water, acetone, diisobutyl ketone, THF, ethyl acetate, dioxane, acetonitrile, chloroform, dichloromethane, dichloroethylene, pyridine, dimethylaniline, DMF, DMAC, DMSO, etc., as well as mixtures of such solvents. While the reaction temperature is virtually optional, the reaction is generally conducted under cooling or at room temperature. When the reaction proceeds with liberation of an acid, a base is added to the reaction system as necessary. The base used for this purpose is exemplified by aliphatic, aromatic or heterocyclic nitrogen containing bases such as triethylamine, N,N-dimethylaniline, N-ethylmorpholine, pyridine, collidine, 2,6-lutidine, etc. alkali metal carbonates such as sodium carbonate, potassium carbonate etc., and alkali metal bicarbonate such as potassium hydrogen carbonate, sodium hydrogen carbonate, etc. When the acylation reaction proceeds dehydratingly, it is preferable to remove water from the solvent. In some instances, the reaction is conducted under moisture-free conditions, e.g. in an inert gaseous atmosphere such as nitrogen gas.

When the reaction product has a protective group, the protective group is removed by a per se known procedure.

The compound [I] or a salt thereof can also be produced by the following procedure. Thus, the compound [V] is reacted with a 4-halo-3-oxobutyryl halide, which is obtained by reacting diketene with a halogen (e.g. chlorine or bromine) in an equimolar ratio, to give a compound of the general formula:

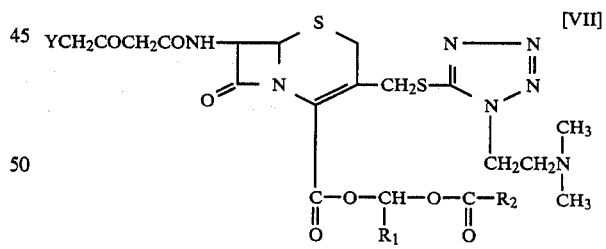

[wherein Y is a halogen atom; $R_1$ and $R_2$ have the same meaning as defined hereinbefore], which is then reacted with thiourea. In the above general formula [VII], the halogen atom Y is for example chlorine or bromine.

The reaction of the compound [V] with 4-halo-3-oxobutyryl halide may be carried out by methods known per se, e.g., the method disclosed in U.S. Pat. No. 4,080,498.

In the reaction of the compound [VII] with thiourea, thiourea is preferably used as it is but may be used in the form of a salt with an alkali metal such as lithium, sodium and potassium, or ammonium salt. Generally the reaction is carried out using the two reactants in an equimolar ratio in a solvent and, in some instances, can be conducted in the presence of 1 to 2 molar equivalents of a base if necessary. Preferred examples of said solvent include water, methanol, ethanol, acetone, dioxane, acetonitrile, chloroform, ethylene chloride, THF, ethyl acetate, DMF, DMAC, DMSO, etc. Among these solvents, hydrophilic solvents can be used in admixture with water. Preferred examples of said base include alkali metal hydroxides such as sodium hydroxide, potassium hydroxide, etc., alkali metal carbonates such as sodium carbonate, potassium carbonate, etc., alkali metal hydrogen carbonates such as sodium hydrogen carbonate, etc., and organic tertiary amines such as triethylamine, trimethylamine, pyridine etc. While there is virtually no limitation on the reaction temperature, generally the reaction is preferably conducted under cooling. The reaction generally proceeds at a fast rate and goes to completion within 10 minutes, although a reaction time in excess of 30 minutes is at times required. The compound [VII] can be easily produced by the above-described process or other processes known per se.

The compound [I] or a salt thereof can also be produced by reacting a compound of the general formula:

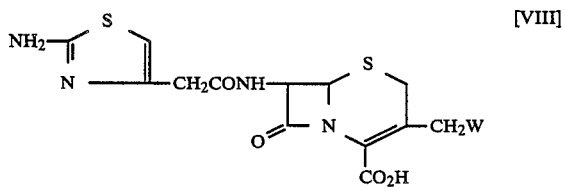

[wherein W is acetoxy, acetoacetoxy or a halogen atom or a carbamoyloxy] or a salt thereof with the compound [III] in the same manner as the esterification reaction described hereinbefore and reacting the resulting compound of the general formula:

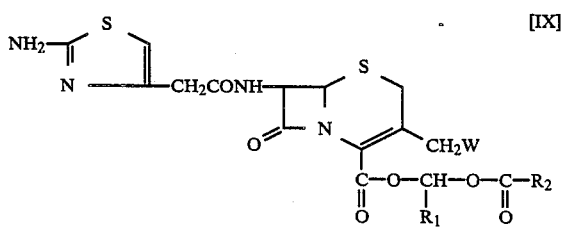

[wherein symbols have the same meanings as defined hereinbefore] or a salt thereof with 1-(2-dimethylaminoethyl)-5-mercapto-1H-tetrazole. Referring to the above general formulas [VIII] and [IX], the halogen atom W is, for example, chlorine, bromine and iodine. In this reaction, the starting material 1-(2-dimethylaminoethyl)-5-mercapto-1H-tetrazole is used in an approximately equimolar proportion with respect to the compound [IX].

This reaction can generally be conducted smoothly in a solvent. Examples of such solvent include water, THF, ethyl acetate, dioxane, acetonitrile, chloroform, dichloromethane, DMF, DMAC, DMSO, etc. When water is used, it can be used in admixture with a highly water-miscible solvent. Generally, this reaction is conducted in the presence of a base. Preferred examples of the base are weak bases such as alkali metal carbonates (e.g. sodium carbonate, potassium carbonate etc.), alkali metal bicarbonate (e.g. sodium hydrogen carbonate, potassium hydrogen carbonate, etc.). The base is used in an approximately equimolar proportion with respect to the starting compound, 1-(2-dimethylaminoethyl)-5-mercapto-1H-tetrazole. While the reaction temperature is more or less optional, the reaction is generally conducted at room temperature up to 40° C. through 60° C. The reaction time is about 30 minutes to about 3 hours, depending on the species of solvent and the reaction temperature.

If the compound [I] or a salt thereof prepared as above contains its $\Delta^2$-isomer, the isomer can be converted to the compound [I] or a salt thereof by, for example, isomerizing the isomer to the $\Delta^3$-isomer by a per se known method [Journal of Medicinal Chemistry, Vol. 18, 986 (1975)], or converting the isomer to the $\Delta^3$-isomer via a corresponding S-oxide derivative and reducing it.

When the product compound [I] is produced in the form of free compound, it can be converted to a salt thereof by dissolving the free compound in an inert solvent such as dichloromethane and chloroform, and adding about 1 to 10 mole equivalents of an acid to the solution. When the compound [I] is produced in the form of an acid addition salt, it can be converted to the form of free base according to a per se known procedure. When the compound [I] or a salt thereof is produced in the form of a racemic compound, it can be subjected to the optical resolution according to a per se known procedure to isolate the optically active compounds (D- and L-isomers). The resulting compound [I] or a salt thereof can be isolated and purified by per se known procedures such as solvent extraction, pH adjustment, solvent transformation, crystallization, recrystallization and chromatography.

The starting compound [III] is produced by per se known processes. Further, the compound of general formula [III] wherein X is iodine, i.e. iodoalkyl acylate, can be produced by reacting an acid chloride [X] with an aldehyde derivative [XI] in the presence of a Lewis acid (first step of reaction) and then reacting the resulting chloroalkyl acylate (the compound [III] wherein X is chlorine) with sodium iodide (second step of reaction). (See the reaction formula below)

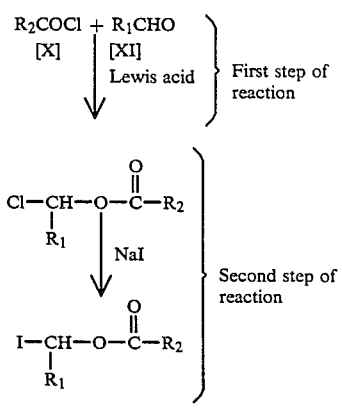

[In the above formulae, $R_1$ and $R_2$ are as defined hereinbefore]

The compounds [X] and [XI] can be produced according to the per se known method. The above first-step reaction is conducted in the presence of a Lewis acid such as anhydrous zinc chloride, aluminum chloride, tin chloride, etc. This reaction proceeds under cooling at about −40° C. to 30° C., preferably at about −40° C. to 0° C. or under heating at about 30° C. to 140° C., preferably at about 90° to 140° C. While the reaction time varies with the reaction temperature, it is generally about 1 to 3 hours under cooling and about 1 to 6 hours under heating. This reaction can proceed even in the absence of a solvent.

Following completion of the above first-step reaction, the reaction mixture is subjected to distillation, column chromatography, etc. to isolate the chloroalkyl acylate (the compound [III] wherein X is chlorine). This compound is then reacted with sodium iodide to give the desired iodoalkyl acylate (second-step reaction). This second-step reaction is conducted in the presence of the common solvent such as acetone; acetonitrile, DMF, DMSO, etc. The reaction temperature may be room temperature or a slightly elevated temperature of about 40° to 50° C. The reaction time is about 15 minutes to 6 hours, preferably about 15 minutes to 2 hours.

The reaction product can be isolated and purified by per se known procedures such as solvent extraction, pH adjustment, distillation, distillation under reduced pressure, solvent transformation, chromatography, etc.

When the compound [X] in the form of a racemic mixture is subjected to the following reaction, the resulting compound [III] (wherein X is chlorine or iodine) is also produced in the form of racemic mixture.

The following Reference Examples, Examples, Formulation Examples and Experimental Example are further illustrative but by no means limitative of this invention.

The symbols used in these Reference Examples and Examples have the meanings defined below.

s: singlet; b.s: broad singlet; d: doublet; d.d: double-doublet; t: triplet; q: quartet; ABq: AB-pattern quartet; m: multiplet

REFERENCE EXAMPLE 1

1-Iodo-2-methylpropyl cyclohexanecarboxylate (a) In 45 g of cyclohexanecarbonyl chloride is added a catalyst amount of anhydrous zinc chloride and the mixture is cooled to −20° C. With stirring 25 g of isobutylaldehyde is added dropwise to the mixture, and the mixture is stirred at the same temperature for an hour and then at 5° C. for 2 hours. The reaction mixture is subjected to column chromatography on silica gel (Kieselgel ®60, 230–400 mesh, E. Merck AG, West Germany), elution being carried out with 1 liter of petroleum ether. The eluate is evaporated under reduced pressure to remove the solvent and the residue is further distilled under reduced pressure to give 40 g of 1-chloro-2-methylpropyl cyclohexanecarboxylate as colorless oil.

bp 120–123° C./18 mm Hg.

IR$\nu_{max}^{liquid\ film}$ cm$^{-1}$: 1765, 1750.

NMR(CDCl$_3$)δ: 1.00(d,J=8 Hz, 6H), 1.10–2.0(m, 11H), 2.10–2.40(m, 1H), 6.30(d,J=5 Hz, 1H).

(b) Acetonitrile (200 ml) is warmed to 60° C., and 33 g of sodium iodide is added and dissolved. To this solution is added 13 g of 1-chloro-2-methylpropyl cyclohexanecarboxylate obtained in the above manner (a) and the mixture is stirred for 40 minutes and poured into 500 ml of ice-water. After stirring well, extraction is carried out with hexane. The extract is washed with water and 5% aqueous sodium thiosulfate in that order and dried over anhydrous magnesium sulfate. The solvent is then distilled off under reduced pressure to give 9.0 g of the title compound.

IR$\nu_{max}^{liquid\ film}$ cm$^{-1}$: 1760, 1750.

The compounds obtained in the same manner as Reference Example 1 are listed below.

1-Iodopropyl cyclohexanecarboxylate IR$\nu_{max}^{liquid\ film}$ cm$^{-1}$: 1760, 1740.

1-Iodobutyl cyclohexanecarboxylate IR$\nu_{max}^{liquid\ film}$ cm$^{-1}$: 1760, 1750.

1-Iodo-1-cyclohexylmethyl cyclohexanecarboxylate IR$\nu_{max}^{liquid\ film}$ cm$^{-1}$: 1760, 1750.

1-Iodo-2-methylpropyl cyclohexylacetate IR$\nu_{max}^{liquid\ film}$ cm$^{-1}$: 1760, 1750.

1-Iodo-2-methylpropyl phenylacetate IR$\nu_{max}^{liquid\ film}$ cm$^{-1}$: 1760, 1755.

1-Iodobutyl phenylacetate IR$\nu_{max}^{liquid\ film}$ cm$^{-1}$: 1760, 1755.

REFERENCE EXAMPLE 2

1-Iodo-1-cyclohexylmethyl n-pentanate (a) In 25 g of n-pentanoyl chloride is added a catalyst amount of anhydrous zinc chloride and the mixture is cooled to −20° C. With stirring, 25 g of cyclohexylaldehyde is added dropwise to the mixture, and the mixture is stirred at the same temperature for an hour and then at 5° C. for an hour. The reaction mixture is subjected to column chromatography on silica gel (Kieselgel ®60, 230–400 mesh, E. Merck AG, West Germany), elution being carried out with 500 ml of petroleum ether. The eluate is concentrated under reduced pressure to give 35 g of 1-chloro-1-cyclohexylmethyl n-pentanate as colorless oil.

IR$\nu_{max}^{liquid\ film}$ cm$^{-1}$: 1765, 1750.

(b) Acetonitrile (200 ml) is warmed to 60° C., and 30 g of sodium iodide is added and dissolved. To this solution is added 12 g of 1-chloro-1-cyclohexylmethyl n-pentanate obtained in the above manner (a) and the mixture is stirred at 60° C. for 40 minutes and poured into 500 ml of ice-water. Extraction is carried out with 200 ml of hexane. The extract is washed with water and a 5% aqueous sodium thiosulfate solution in that order and dried over anhydrous magnesium sulfate. The solvent is then distilled off under reduced pressure to give 8.0 g of the title compound.

IR$\nu_{max}^{liquid\ film}$ cm$^{-1}$: 1755, 1740.

The compounds obtained in the same manner as Reference Example 2 are listed below.

1-Iodo-1-cyclohexylmethyl n-butyrate IR$\nu_{max}^{liquid\ film}$ cm$^{-1}$: 1760, 1740.

1-Iodo-1-cyclohexylmethyl 3-methylbutyrate IR$\nu_{max}^{liquid\ film}$ cm$^{-1}$: 1755, 1740.

1-Iodo-1-cyclohexylmethyl n-hexanate IR$\nu_{max}^{liquid\ film}$ cm$^{-1}$: 1760, 1745.

EXAMPLE 1

1-(Cyclohexylcarbonyloxy)-2-methylpropyl 7β-[2-(2-aminothiazol-4-yl)acetamido]-3-[[[1-(2-dimethylaminoethyl) -1H-tetrazol-5-yl]thio]methyl]ceph-3-em-4-carboxylate dihydrochloride (compound No. 1)

In 120 ml of dimethylacetamide is dissolved 6.0 g of potassium 7β[2-(2-aminothiazol-4-yl) acetamido]-3-[[[1-(2-dimethylaminoethyl) -1H-tetrazol-5-yl]thio]methyl]ceph-3-em-4-carboxylate and the solution is cooled to 0° C. With stirring, 9.0 g of 1-iodo-2-methylpropyl cyclohexanecarboxylate is added at one stroke to the solution, followed by stirring for further 10 minutes. To the reaction mixture is added 70 ml of 2 N HCl-ether, followed by addition of 300 ml of ether. The ether layer is discarded and the residue is dissolved in 50 ml of 1 N hydrochloric acid and subjected to column chromatography on XAD-II ®resin (Rohm & Haas Co. U.S.A.), elution being carried out with water-acetonitrile (3:1). The fractions containing the desired product are combined, evaporated under reduced pressure to remove the solvent and lyophilized to give 2.5 g of the title compound as a colorless powder.

IR$\nu_{max}^{KBr}$ cm$^{-1}$: 1780, 1750, 1680.

NMR(d$_6$-DMSO)θ: 0.90(d,J=8 Hz, 6H), 1.0-2.0(m, 11H), 2.20-2.40(m, 1H), 2.80(s, 6H), 3.60(s, 2H), 3.70-3.60(m, 2H), 4.26(s, 2H), 4.76(t, J=6 Hz, 2H), 5.10(d, J=4.5 Hz, 1H), 5.70(d.d, J=4.5 Hz 6 Hz, 1H), 6.60(s, 1H), 6.63(d, J=4.5 Hz, 1H), 9.0-9.6(b.s, 1H), 9.20(d, J=6 Hz, 1H).

Elemental analysis for $C_{29}H_{41}N_9O_6S_3 \cdot 2HCl \cdot 2H_2O$. Calcd.(%): C, 42.64; H, 5.81; N, 15.44. Found (%): C, 42.80; H, 5.92; N, 15.59.

EXAMPLE 2

1-(Cyclohexylcarbonyloxy)-1-cyclohexylmethyl 7β-[2-(2-aminothiazol-4-yl) acetamido]-3-[[[1-(2-dimethylaminoethyl) -1H-tetrazol-5-yl]thio]methyl]ceph-3-em-4-carboxylate dihydrochloride (compound No. 2)

In 120 ml of dimethylformamide is dissolved 6.0 g of potassium 7β-[2-(2-aminothiazol-4-yl) acetamido]-3-[[[1-(2-dimethylaminoethyl) -1H-tetrazol-5-yl]thio]methyl]ceph-3-em-4-carboxylate and the solution is cooled to 0° C. With stirring, 10 g of 1-iodo-1-cyclohexylmethyl cyclohexanecarboxylate is added at one stroke to the solution and the mixture is further stirred for 10 minutes. To the reaction mixture is added 300 ml of ice-water and extraction is carried out with 200 ml of ethyl acetate. The organic layer is further extracted with 50 ml of 1 N hydrochloric acid and the extract is subjected to column chromatography on XAD-II® resin (Rohm & Haas Co. U.S.A.), elution being carried out with water-acetonitrile (4:1). The fractions containing the desired product are combined, evaporated under reduced pressure to remove the solvent and lyophilized to give 2.7 g of the title compound as a colorless powder.

IR$\nu_{max}^{KBr}$ cm$^{-1}$: 1780, 1750, 1680. NMR(d$_6$ DMSO)δ: 1.00-2.00(m, 21H), 2.20-2.40(m, 1H), 2.85(s, 6H), 3.63(s, 2H), 3.70-4.30(m, 2H), 4.70(t, J=6 Hz, 2H), 5.15(d, J=4.5 Hz, 1H), 5.75(d.d, J=4.5 Hz and 9 Hz), 6.63(s, 1H), 9.10-9.60(b.s, 1H), 9.25(d, J=9 Hz, 1H).

Elemental analysis for $C_{32}H_{45}N_9O_6S_3 \cdot 2HCl \cdot 2H_2O$, Calcd.(%): C, 44.85; H, 6.00; N, 14.71. Found (%) C, 44.98; H, 6.01; N, 15.02.

The compounds obtained in the same manner as Example 2 are listed below in Examples 3-7 together with their physico-chemical constants.

EXAMPLE 3

1-(Cyclohexylcarbonyloxy)propyl 7β-[2-(2-amino-thiazol-4-yl)acetamido]-3-[[[1-(2-dimethylaminoethyl) -1H-tetrazol-5-yl]thio]methyl]ceph-3-em-4-carboxylate dihydrochloride(compound No. 3)

IR$\nu_{max}^{KBr}$ cm$^{-1}$: 1780, 1750, 1680.

NMR(d$_6$-DMSO)δ: 0.90(t,J=8.5 Hz, 3H), 1.20-2.00(m, 12H), 2.20-2.60(m, 1H), 2.90(s, 6H), 3.65(s, 2H), 3.70-3.80(m, 1H), 4.20-4.50(m, 1H), 4.80(t,J=6.5 Hz, 2H), 5.20(d,J=4.5 Hz, 1H), 5.75(d.d,J=4.5 Hz and 9 Hz, 1H), 6.66(s, 1H), 6.80-7.00(m, 1H), 9.10-9.70(b.s, 1H), 9.35(d,J=9 Hz, 1H).

Elemental analysis for $C_{28}H_{37}N_9O_6S_3 \cdot 2HCl \cdot 5/2H_2O$: Calcd.(%): C41.53, H5.48, N15.57. Found (%) C41.66, H5.52, N15.48.

EXAMPLE 4

1-(Cyclohexylcarbonyloxy)butyl 7β-[2-(2-aminothiazol-4-yl)acetamido]-3-[[[1-(2-dimethylaminoethyl) -1H-tetrazol-5-yl]thio]methyl]ceph-3-em-4-carboxylate dihydrochloride(compound No. 4)

IR$\nu_{max}^{KBr}$ cm$^{-1}$: 1780, 1750, 1680.

NMR(d$_6$-DMSO)δ: 0.95(t,J=7.5 Hz, 3H), 1.10-2.00(m, 14H), 2.20-2.50(m, 1H), 2.90(s, 6H), 3.80(s, 2H), 3.70-3.90(m, 2H), 4.30-4.50(m, 2H), 4.83(t,J=6 Hz, 2H), 5.20(d,J=4.5 Hz, 1H), 5.75(d.d,J=4.5 Hz and 9 Hz, 1H), 6.70(s, 1H), 6.80-7.03(m, 1H), 9.20-9.90(b.s, 1H), 9.33(d,J=9 Hz, 1H).

Elemental analysis for $C_{29}H_{41}N_9O_6S_3 \cdot 2HCl \cdot 3/2H_2O$: Calcd.(%): C43.66, H4.55, N15.80. Found (%): C43.47, H4.82, N15.48.

EXAMPLE 5

1-(Cyclohexylacetoxy)-2-methylpropyl 7β-[2-(2-aminothiazol-4-yl)acetamido]-3-[[[1-(2-dimethylaminoethyl) 1H-tetrazol-5-yl]thio]methyl]ceph-3-em-4-carboxylate dihydrochloride (compound No. 5)

IR$\nu_{max}^{KBr}$ cm$^{-1}$: 1780, 1760, 1750, 1675. NMR(d$_6$-DMSO)δ: 0.96(d,J=6 Hz, 6H), 1.00-1.80(m, 10H), 2.20(d,J=6 Hz, 2H), 2.83(s, 6H), 3.63(s, 2H), 3.70-3.80(m, 2H), 4.20-4.40(m, 2H), 4.80(t,J=6 Hz, 2H), 5.03(d,J=4.5 Hz, 1H), 5.80(d.d,J=4.5 Hz 9 Hz, 1H), 6.63(s, 1H), 6.70-6.80(m, 1H), 9.20-10.0(b.s, 1H), 9.30(d,J=9 Hz, 1H).

Elemental analysis for $C_{30}H_{43}N_9O_6S_3 \cdot 2HCl \cdot 3/2H_2O$: Calcd.(%): C43.84, H5.89, N15.34. Found (%): C43.89, H5.82, N15.13.

EXAMPLE 6

1-(Phenylacetoxy)-2-methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride (compound No. 6)

IR$\nu_{max}^{KBr}$ cm$^{-1}$: 1780, 1750, 1690.

NMR(d$_6$-DMSO)δ: 0.90(d,J=7.5 Hz), 1.90-2.20(m, 1H), 2.80(s, 6H), 3.66(s, 2H), 3.70-3.90(m, 2H), 4.20-4.40(m, 2H), 5.80(t,J=6 Hz, 2H), 5.13(d,J=4.5 Hz, 1H), 5.73(d.d,J=4.5 Hz 9 Hz, 1H), 6.60(s, 1H), 6.80-7.03(m, 1H), 7.30(s, 5H), 9.10-10.0(b.s, 1H), 9.30(d,J=9 Hz, 1H).

Elemental analysis for $C_{30}H_{37}N_9O_6S_3 \cdot 2HCl \cdot 2H_2O$: Calcd.(%): C43.69, H5.25, N15.28. Found (%): C43.74, H5.15, N15.11.

EXAMPLE 7

1-(Phenylacetoxy)butyl 7β-[2-(2-aminothiazol-4-yl) acetamido]-3-[[[1-(2-dimethylaminoethyl)-1H-tetrazol-5-yl]thio]methyl]ceph-3-em-4-carboxylate dihydrochloride IR$\nu_{max}^{KBr}$ cm$^{-1}$: 1780, 1750, 1680.

NMR(d$_6$-DMSO)δ: 0.90(t,J=6 Hz), 1.20-1.50(m, 2H), 1.66-1.90(m, 1H), 2.83(s, 6H), 3.66(s, 2H), 3.70-3.80(m, 2H), 4.20-4.50(m, 2H), 4.80(t,J=6 Hz, 2H), 5.16(d,J=4.5 Hz, 1H), 5.73(d.d,J=4.5 Hz 9 Hz, 1H), 6.66(s, 1H), 6.80-7.03(m, 1H), 7.30(s, 5H), 9.10-9.90 (b.s, 1H), 9.30(d,J=9 Hz, 1H).

Elemental analysis for $C_{30}H_{37}N_9O_6S_3 \cdot 2HCl \cdot 3/2H_2O$:
Calcd.(%): C44.17, H5.19, N15.45. Found (%): C44.23, H5.05, N15.34.

EXAMPLE 8

1-(Cyclohexylcarbonyloxy)-2-methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride (Compound No. 1)

(a) Production of 1-(cyclohexylcarbonyloxy)-2-methylpropyl 7β-amino-3-[[[1-(2-dimethylaminoethyl)-1H-tetrazol-5-yl]thio]methyl]ceph-3-em-4-carboxylate dihydrochloride.

To 60 ml of dimethylformamide solution containing 4.22 g of 7β-amino-3-[[[1-(2-dimethylaminoethyl)-1H-tetrazol-5-yl]thio]methyl]ceph-3-em-4-carboxylic acid dihydrochloride is added 1.67 g of potassium acetate.

The mixture is cooled to 0° C. With stirring, 5.0 g of 1-iodo-2-methylpropylcyclohexane carboxylate is added dropwise to the solution, followed by stirring at 0° C. for 5 minutes. The reaction mixture is poured into a mixture of 60 ml of methylene chloride and 60 ml of 0.1 N-HCl and the aqueous layer is separated. The aqueous solution is adjusted to pH 6.0 with a saturated aqueous sodium bicarbonate solution and extracted with methylene chloride. To the methylene chloride solution is added water and the mixture is adjusted to pH 2.0 with 4N-HCl. The aqueous layer is separated and the remaining methylene chloride is removed under reduced pressure. Then, the aqueous solution islyophilized to obtain 2.5 g of the title compound.

IR$\nu_{max}^{nujol}$ cm$^{-1}$: 1780, 1750, 1670.

(b) Production of 1-(cyclohexylcarbonyloxy)-2-methylpropyl 7β-[2-(2-aminothiazol-4-yl)acetamido][[1-(2-dimethylaminoethyl)-1H-tetrazol-5-yl]thio]methyl]ceph-3-em-4-carboxylate dihydrochloride To a mixture of 30 ml of water and 30 ml of methylene chloride is added 1.8 g of the compound obtained in the above (a), followed by addition of 0.55 g of sodium bicarbonate with stirring. The organic layer is separated and dried over anhydrous calcium chloride. After removal of the drying agent by filtration, is added to the filtrate a 20 ml of dimethylformamide solution containing 0.60 g of (2-aminothiazol-4-yl)acetic acid hydrochloride and 0.62 g of dicyclohexylcarbodiimide, followed by stirring the mixture at room temperature. The resulting precipitates are removed by filtration and 150 ml of ethyl acetate and 100 ml of ice cooled water are added to the filtrate. The organic layer is separated, washed with water and a saturated aqueous sodium chloride solution and is dried over anhydrous magnesium sulfate. After removal of drying agent by filtration, the filtrate is concentrated to 10 ml under reduced pressure, followed by addition of an anhydrous ethereal hydrogen chloride solution. The resulting precipitates are collected by filtration to obtain 0.3 g of white powder.

This product shows the same NMR and IR spectra as those of the product obtained in Example 1.

EXAMPLE 9

1-(Cyclohexylcarbonyloxy)-2methylpropyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride (Compound No. 1)

To a mixture of 15 ml of water and 15 ml of methylene chloride is added 1.2 g of 1-(cyclohexylcarbonyloxy)-2-methylpropyl 7β-amino-3-[[[1-(2-dimethylaminoethyl)-1H-tetrazol-5-yl]ceph-3-em-4-carboxylate dihydrochloride obtained in Example 8 (a) and the mixture is stirred together with 0.30 g of sodium bicarbonate. The organic layer is separated and dried over anhydrous calcium chloride. Then, the solvent is distilled off under reduced pressure. The residue is dissolved in 15 ml of methylene chloride and the solution is cooled to −25° C. To this solution is added 2.0 ml of methylene chloride solution containing 0.5 g of 4-chloroacetoacetyl chloride and the mixture is stirred at −20° C. to −15° C. for 20 minutes. Then, 0.76 g of thiourea and 5 ml of dimethylacetamide are added and the mixture is stirred at room temperature for 3 hours. Water is added to the reaction mixture and the aqueous layer is separated. The aqueous solution is adjusted to pH 6.0 and extracted with methylene chloride. The methylene chloride layer is admixed with water and adjusted to pH 1.5 with 2N-HCl. The aqueous layer is separated and the remaining methylene chloride is distilled off under reduced pressure. The aqueous solution is subjected to column chromatography on Amberlite XAD-II® (produced by Rohm & Haas Co., U.S.A.), elution being carried out with 120 ml of 0.1 N-HCl and then with 20% acetonitrile-0.01N-HCl. The eluate is lyophilized to obtain 0.5 g of white powder. This product shows the same NMR and IR spectra as those of the product obtained in Example 1.

EXAMPLE 10

1-(Cyclohexylcarbonyloxy)-2-methylpropyl 7β-[2-(2-aminothaizol-4-yl)acetamido]-3-[[[1-(2-dimethylaminoethyl)-1H-tetrazol-5-yl]thio]methyl]ceph-3-em-4-carboxylate dihydrochloride(Compound No. 1)

(a) Production of 1-(cyclohexylcarbonyloxy)-2-methylpropyl 7β-[2-(2-aminothiazol-4-yl)acetamido]-3-acetoacetoxymethyl-ceph-3-em-4-carboxylate In 30 ml of N,N-dimethylformamide is dissolved 4.76 g of sodium 7β-[2-(2-aminothiazol-4-yl)acetamido]-3-acetoacetoxymethyl-ceph-3-em-4-carboxylate and the solution is cooled to −5° C. With stirring, 5.0 g of 1-iodo-2-methylpropylcyclohexane carboxylate is added dropwise, followed by stirring for further 5 minutes. Thereafter, following the procedure of Example 1, 2.5 g of the title compound is obtained.

IR$\nu_{max}^{KBr}$ cm$^{-1}$: 1780, 1750, 1680.

NMR($d_6$-DMSO)δ: 0.90(d,J=8 Hz, 6H), 1.0–2.0(m, 11H), 2.10(s, 3H), 2.20–2.40(m, 1H), 3.60(s, 2H), 3.60–3.70(m, 2H), 4.76(t,J=6 Hz, 2H), 5.10(d,J=4.5 Hz, 1H), 5.70(d.d,J=4.5 Hz 6 Hz, 1H), 6.60(s, 1H), 6.63(d,J=4.5 Hz, 1H), 9.0–9.6(b.s, 1H), 9.20(d,J=6 Hz, 1H).

(b) Production of 1-(cyclohexylcarbonyloxy)-2-methylpropyl 7β-[2-(2-aminothiazol-4-yl)acetamido-3-[[[1-(2-dimethylaminoethyl)-1H-tetrazol-5-yl]thio]methyl] ceph-3-em-4-carboxylate dihydrochloride To 30 ml of an acetone solution containing 2.3 g of the compound obtained in the above (a) is added 10 ml of an aqueous solution containing 0.9 g of 1-(2-dimethylaminoethyl)-5-mercapto-1H-tetrazole and 0.8 g of sodium bicarbonate and the mixture is heated to 40° C. for one hour with stirring. The reaction mixture is poured into a mixture of 150 ml of ethyl acetate and 50 ml of ice water and the organic layer is separated. The organic layer is washed with ice water and then with saturated aqueous sodium chloride and dried over anhydrous magnesium sulfate. Thereafter, the solvent is distilled off under reduced pressure. The residue is dissolved in 5 ml of 0.01N-HCl and insoluble matter is removed by filtration. The filtrate is lyophilized to obtain 0.05 g of the title compound of white powder.

This product shows the same NMR and IR spectra as those of the product obtained in Example 1.

EXAMPLE 11

1-n-Pentanoyloxy-1-cyclohexylmethyl 7β-[2-(2-aminothiazol-4-yl)acetamido]-3-[[[1-(2-dimethylaminoethyl)-1H-tetrazol-5-yl]thio]methyl]ceph-3-em-4-carboxylate dihydrochloride (compound No. 7)

In 120 ml of dimethylacetamide is dissolved 6.0 g of potassium 7β-[2-(2-aminothiazol-4-yl)acetamido]-3-[[[1-(2-dimethylaminoethyl)-1H-tetrazol-5-yl]thio]-methyl]-ceph-3-em-4-carboxylate and the solution is to 2C. With stirring, 8.0 g of 1-iodo-1-cyclohexylmethyl n-pentanate is added at one stroke to the solution, followed by stirring for further 10 minutes. To the reaction mixture is added 70 ml of 2 N HCl-ether, followed by addition of 300 ml of ether. The separating ether layer is removed and the residue is dissolved in 50 ml of 1 N hydrochloric acid and subjected to column chromatography on XAD-II ® resin (Rohm & Haas Co., U.S.A.), elution being carried out with acetonitrile-water (1:2). The fractions containing the desired product are combined, evaporated under reduced pressure to remove the solvent and lyophilized to give 2.1 g of the title compound as a colorless powder.

IR$\nu_{max}^{KBr}$ cm$^{-1}$: 1780, 1750, 1680.

NMR(d$_6$-DMSO)δ: 0.90(t,J=7 Hz, 3H), 1.05-1.90(m, 16H), 2.40(t,J=6 Hz, 2H), 2.90(s, 6H), 3.65(s, 2H), 3.80-3.90(m, 2H), 4.35(s, 2H), 4.80(t,J=6 Hz,2H), 5.20(d,J=5 Hz, 1H), 5.65-5.85(m, 1H), 6.60-6.80(m, 1H), 6.65(s, 1H), 9.10-9.70(b.s, 1H), 9.30(d,J=9 Hz,1H)

Elemental analysis for C$_{30}$H$_{43}$N$_9$O$_6$S$_3$·2HCl·3H$_2$O: Calcd.(%): C, 42.45; H, 6.06; N, 14.85. Found (%): C, 42.56; H, 5.69; N, 15.07.

EXAMPLE 12

1-n-Butyryloxy-1-cyclohexylmethyl 7β-[2-(2-aminothiazol-4-yl) acetamido]-3-[[[1-(2-dimethylaminoethyl) -1H-tetrazol-5-yl]thio]methyl]ceph-3-em-4-carboxylate dihydrochloride(Compound No. 8) is obtained according to the same procedure as Example 11.

IR$\nu_{max}^{KBr}$ cm$^{-1}$: 1780, 1750, 1680.

NMR(d$_6$-DMSO)δ: 0.90(t,J=7.5 Hz, 3H), 1.01-1.90(m, 13H), 2.30(t,J=6 Hz, 2H), 2.90(s, 6H), 3.60-3.90(m, 6H), 4.30(s, 2H), 4.80(t,J=6 Hz,2H), 5.20(d,J=5 Hz, 1H), 5.60-5.80(m, 1H), 6.60(s, 1H), 6.60-6.80(m, 1H), 9.0-9.60(b.s, 1H), 9.20(d,J=9 Hz, 1H).

Elemental analysis for C$_{29}$H$_{41}$N$_9$O$_6$S$_3$·2HCl·3H$_2$O: Calcd.(%): C41.73, H5.92, N15.10. Found (%): C41.47, H5.70, N15.31.

EXAMPLE 13

1-(3-Methylbutyryloxy)-1-cyclohexylmethyl 7β-[2-(2-amino-thiazol-4-yl) acetamido]-3-[[[1-(2-dimethylaminoethyl))-1H-tetrazol-5-yl]thio]methyl]ceph-3-em-4-carboxylate dihydrochloride (compound No. 9) is obtained according to the same procedure as Example 11

IR$\nu_{max}^{KBr}$ cm$^{-1}$: 1780, 1750, 1680.

NMR(d$_6$-DMSO)δ: 0.90(d,J=6 Hz, 6H), 1.03-1.90(m, 11H), 2.20(d,J=6 Hz,2H), 2.90(s, 6H), 3.40-3.90(m, 6H), 4.40(s, 2H), 4.85(t,J=6 Hz, 2H), 5.20(d,J=5 Hz, 1H), 5.70-5.90(m, 1H), 6.70(s, 1H), 6.70-6.85(m, 1H), 8.90-9.70(b.s, 1H), 9.30(d,J=9 Hz, 1H).

Elemental analysis for C$_{30}$H$_{43}$N$_9$O$_6$S$_3$·2H$_2$O: Calcd.(%): C42.46, H6.06, N14.85. Found (%) C42.60, H6.21, N14.57.

EXAMPLE 14

1-n-Hexanoyloxy-1-cyclohexylmethyl 7β-[2-(2-aminothiazol-4-yl)acetamido]-3-[[[1-(2-dimethylaminoethyl) -1H-tetrazol-5-methyl]ceph-3-em-4-carboxylate dihydrochloride (compound No. 10) is obtained according to the same procedure as Example 11

IR$\nu_{max}^{KBr}$ cm$^{-1}$: 1780, 1750, 1675.

NMR(d$_6$-DMSO)δ: 0.85(t,J=6 Hz, 3H), 1.05-1.90(m, 16H), 2.40(t,J=6 Hz, 2H), 2.90(s, 6H), 3.60-3.80(m, 6H), 4.35(s, 2H), 4.80(t,J=6 Hz, 2H), 5.15(d,J=5 Hz, 1H), 5.70-5.90(m, 1H), 6.70(s, 1H), 6.70-6.90(m, 1H), 8.90-9.70(b.s, 1H), 9.30(d,J=9 Hz, 1H).

Elemental analysis for C$_{31}$H$_{45}$N$_9$O$_6$S$_3$·2HCl·3H$_2$O: Calcd.(%): C43.16, H6.19, N14.61. Found (%): C42.89, H6.01, N14.73.

FORMULATION EXAMPLE 1

Compound No. 1 [388 g; 250 g in terms of the non-ester (compound [II])] as obtained in Example 1 is evenly admixed with 70.5 g of hydroxypropylcellulose and 70.5 g of carboxymethylcellulose and the mixture is distributed in 264.5 mg portions (125 mg in terms of the non-ester) into capsules in the conventional manner.

FORMULATION EXAMPLE 2

Compound No. 1 [388 g; 250 g in terms of the non-ester (compound [II])] as obtained in Example 1 is evenly admixed with 70 g of starch and 6 g of hydroxypropylcellulose and the mixture is tableted in the conventional manner to provide 232 mg tablets (125 mg in terms of the non-ester).

FORMULATION EXAMPLE 3

Compound No. 7 [403 g; 250 g in terms of the non-ester (compound [II])] as obtained in Example 11 is evenly admixed with 70.5 g of hydroxypropylcellulose and 70.5 g of carboxymethylcellulose and the mixture is distributed in 272 mg portions (125 mg in terms of the non-ester) into capsules in the conventional manner.

FORMULATION EXAMPLE 4

Compound No. 7 [403 g; 250 g in terms of the non-ester (compound [II])] as obtained in Example 11 is evenly admixed with 70 g of starch and 6 g of hydroxypropylcellulose and the mixture is tableted in the conventional manner to provide 266.5 mg tablets (125 mg in terms of the non-ester).

EXPERIMENTAL EXAMPLE

The compounds of Examples (compound Nos. 1, 2, 3, 4, 5, 6, 7 and 8) and, as a control compound, the pivaloyloxymethyl ester of compound [II] (hereinafter referred to briefly as compound A) are administered orally to mice, each compound to one animal, in the dose of 100 mg/kg in terms of the non-ester, i.e. compound [II]. At 0.25, 0.5, 1.0 and 2.0 hours after administration, the concentration of compound [II] in the plasma of each mouse is measured by the cup method using *Proteus mirabilis* Eb 313 as the test organism and the area under plasma concentration-time curve from zero to 2 hours (AUC) is calculated. As a control, compound [II] is subcutaneously administered to a mouse and the AUC value is calculated as above. The bioavailability is calculated by means of the following equation.

$$\text{Bioavailability (\%)} = \frac{AUC\,(p.o.)}{AUC\,(s.c.)} \times 100$$

TABLE 1

| Compound No. | Plasma level of non-ester (compound [II]) (μg/ml), n = 3* | | | | AUC (μg · hr/ ml) | Bioavailability (%) |
| --- | --- | --- | --- | --- | --- | --- |
| | 0.25 hr | 0.5 hr | 1.0 hr | 2.0 hr | | |
| 1 | 66.3 | 34.5 | 8.9 | 0.9 | 36.6 | 94.4 |
| 2 | 46.1 | 32.2 | 21.2 | 4.7 | 41.9 | 107.8 |
| 3 | 59.5 | 25.0 | 11.7 | 1.0 | 33.5 | 86.4 |
| 4 | 47.0 | 38.4 | 14.4 | 2.8 | 38.4 | 98.8 |
| 5 | 29.2 | 46.7 | 11.1 | 2.6 | 34.5 | 88.8 |
| 6 | 35.1 | 32.3 | 15.7 | 2.4 | 33.9 | 87.2 |
| 7 | 36.4 | 30.0 | 17.0 | 3.2 | 34.5 | 88.9 |
| 8 | 50.0 | 39.6 | 15.6 | 2.33 | 40.2 | 103.5 |
| A | 21.0 | 16.2 | 6.1 | 0.6 | 16.2 | 41.8 |
| Control: Subcutaneous administration of compound [II] | 69.2 | 29.0 | 13.2 | 1.5 | 38.8 | 100 |

*Average for 3 mice

We claim:

1. A compound, namely 1-(phenylacetoxy)-2-methylpropyl 7β-[2-(2-aminothiazol-4-yl)acetoamido]-3-[[[1-(2-dimethylaminoethyl)-1H-tetrazol-5-yl]thio]methyl]-ceph-3-em-4-carboxylate, or a pharmaceutically acceptable salt thereof.

2. A compound, namely 1-(cyclohexylcarbonyloxy)-2-methylpropyl-7β-[2-aminothiazol-4-yl)acetoamido]-3-[[[1-(2-dimethylaminoethyl)-1H-tetrazzol-5-yl]thio]methyl]ceph-3-em-4-carboxylate, or a pharmaceutically acceptable salt thereof.

3. A compound, namely 1-(cyclohexylcarbonyloxy)1-cyclohexylmethyl7β-[2-(2-aminothiazol-4-yl)acetoamido]-3-[[[1-(2-dimethylaminoethyl)-1H-tertrazol-5-yl]thio]methyl]ceph-3-em-4-carboxylate, or a pharmaceutically acceptable salt thereof.

4. A compound, namely 1-(cyclohexylcarbonyloxy)-butyl 7β-[2-(2-aminothiazol-4-yl)acetoamido]-3-[[[1-(2-dimethylaminoethyl)-1H-tetrazol-5-yl-]thio]methyl]-ceph-3-em-4-carboxylate, or a pharmaceutically acceptable salt thereof.

5. A compound, namely 1-n-butyryloxy-1-cyclohexylmethyl 7β-[2-(2-aminothiazol-4-yl)acetoamido]-3-[[[1-2-dimethylaminoethyl)-1H-tetrazol-5-yl]thio]methyl]-ceph-3-em-4-carboxylate, or a pharmaceutically acceptable salt thereof.

6. A pharmaceutical composition for antibacterial use comprising an antibacterially effective amount of a compound as defined in claim 1, 2, 3, 4 or 5.

* * * * *